US00PP36801P2

(12) United States Plant Patent
Nontaswatsri

(10) Patent No.: US PP36,801 P2
(45) Date of Patent: Jul. 1, 2025

(54) ***CURCUMA* PLANT NAMED 'Maejo White Pearl'**

(50) Latin Name: ***Curcuma alismatifolia* x *aurantiaca***
Varietal Denomination: Maejo White Pearl

(71) Applicant: Maejo University, Chiang Mai (TH)

(72) Inventor: Chalermsri Nontaswatsri, Chiang Mai (TH)

(73) Assignee: Maejo University (TH)

( * ) Notice: Subject to any disclaimer, the term of this patent is extended or adjusted under 35 U.S.C. 154(b) by 0 days.

(21) Appl. No.: 18/759,605

(22) Filed: Jun. 28, 2024

(51) Int. Cl.
*A01H 5/02* (2018.01)
*A01H 6/00* (2018.01)

(52) U.S. Cl.
USPC ..... Plt./421

(58) Field of Classification Search
USPC ..... Plt./263.1, 421
See application file for complete search history.

(56) References Cited

PUBLICATIONS

Tenan, Shinmei. 2020. Maejo Univeristy Launches Three New Curcuma (Siam Tulip) Varieties. New from Shinmeiten-an in Chiang Mai. http://chaocnx.seesaa.net/article/477971728.html. (Year: 2020).*

* cited by examiner

*Primary Examiner* — Karen M Redden

(57) ABSTRACT

A new and distinct cultivar of *Curcuma* plant named 'Maejo White Pearl' is described, characterized by light-yellow flowers with a light-purple stomata, and green lower bracts. The new variety is a *Curcuma*, normally used as an ornamental garden or landscape plant.

4 Drawing Sheets

Latin name of the genus and species: *Curcuma alismatifolia* x *aurantiaca.*

Variety denomination: 'MAEJO WHITE PEARL'.

BACKGROUND OF THE INVENTION

The new cultivar, *Curcuma* 'Maejo White Pearl', is a product of a planned breeding program by the inventor. 'Maejo White Pearl' is the result of the crossing of the seed parent, an unnamed, unpatented *Curcuma alismatifolia* x *Curcuma aurantiaca*, and the pollen parent, the unpatented *Curcuma* 'Snow White'. The crossing occurred during October 2016, at a nursery in Chiang Mai Province, Thailand. 'Maejo White Pearl' was selected as an interesting new cultivar at the same location in October of 2018.

The first asexual propagation of 'Maejo White Pearl' was performed in October of 2018 by tissue culture at the same nursery in Chiang Mai Province, Thailand, and has been found to retain its distinctive characteristics through successive asexual propagations.

SUMMARY OF THE INVENTION

The cultivar 'Maejo White Pearl' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Maejo White Pearl'. These characteristics in combination distinguish 'Maejo White Pearl' as a new and distinct *Curcuma* cultivar:

1. Light-yellow flowers with a light-purple stomata.
2. Large inflorescence.

3. Green lower bracts.

PARENT COMPARISONS

Plants of the new cultivar 'Maejo White Pearl' are similar to plants of the seed parent in most horticultural characteristics. However, plants of the new cultivar 'Maejo White Pearl' differ in the following:

1. Plants of the new variety are taller than plants of the seed parent.
2. Leaves of the new variety are smaller and narrower than leaves of the seed parent.
3. Flower color of the new variety is light-yellow with a light-purple lip. Flower color of the seed parent is white.
4. Peduncles of the new variety are longer than peduncles of the seed parent.
5. Inflorescence of the new variety is larger than the inflorescence of the seed parent.
6. Lower bracts of the new variety are green, while lower bracts of the seed parent are green with a brown stripe.

Plants of the new cultivar 'Maejo White Pearl' are similar to plants of the pollen parent in most horticultural characteristics. However, plants of the new cultivar 'Maejo White Pearl' differ in the following:

1. Plants of the new variety are larger than plants of the pollen parent.
2. Leaves of the new variety are larger and broader than leaves of the pollen parent.
3. Flower color of the new variety is light-yellow with a light-purple lip. Flower color of the pollen parent is white with a deep purple lip.
4. Peduncles of the new variety are shorter than peduncles of the pollen parent.

5. Inflorescence of the new variety is larger than the inflorescence of the pollen parent.
6. Coma bracts of the new variety are longer than coma bracts of the pollen parent.

COMMERCIAL COMPARISON

'Maejo White Pearl' can be compared to the commercial variety *Curcuma sieboldii* 'Sawasdee-Venus', unpatented. Plants of the new variety are similar to 'Sawasdee-Venus' in most horticultural characteristics, however, 'Maejo White Pearl' differs in the following:

1. Peduncles of the new variety are longer than peduncles of this comparator.
2. Inflorescence of the new variety is larger and longer than the inflorescence of this comparator.
3. Lower bracts of the new variety are green, while lower bracts of this comparator are green with a brown stripe.
4. Leaves of the new variety are smaller and narrower than leaves of this comparator.
5. Flower color of the new variety is light-yellow with a light-purple stomata, while the flower color of this comparator is pinkish-orange.
6. Plants of the new variety are taller than plants of this comparator.

'Maejo White Pearl' can be compared to the co-pending variety *Curcuma* 'Maejo Green Pearl', application Ser. No. 18/759,588. Plants of the new variety are similar to 'Maejo Green Pearl' in most horticultural characteristics, however, 'Maejo White Pearl' differs in the following:

1. Leaf sheaths of the new variety are green; leaf sheaths of this comparator are yellow-green.
2. Lower bracts of the new variety are green with no striping, while lower bracts of this comparator are green with a red-brown stripe.
3. Foliage of the new variety is approximately twice as wide as foliage of this comparator.

BRIEF DESCRIPTION OF THE PHOTOGRAPHS

The accompanying photographs were taken using conventional techniques and although colors may appear different from actual colors due to light reflectance it is as accurate as possible by conventional photographic techniques. All photographs are of a plant of approximately 4 to 5 months of age.

DETAILED BOTANICAL DESCRIPTION

Figure 1:
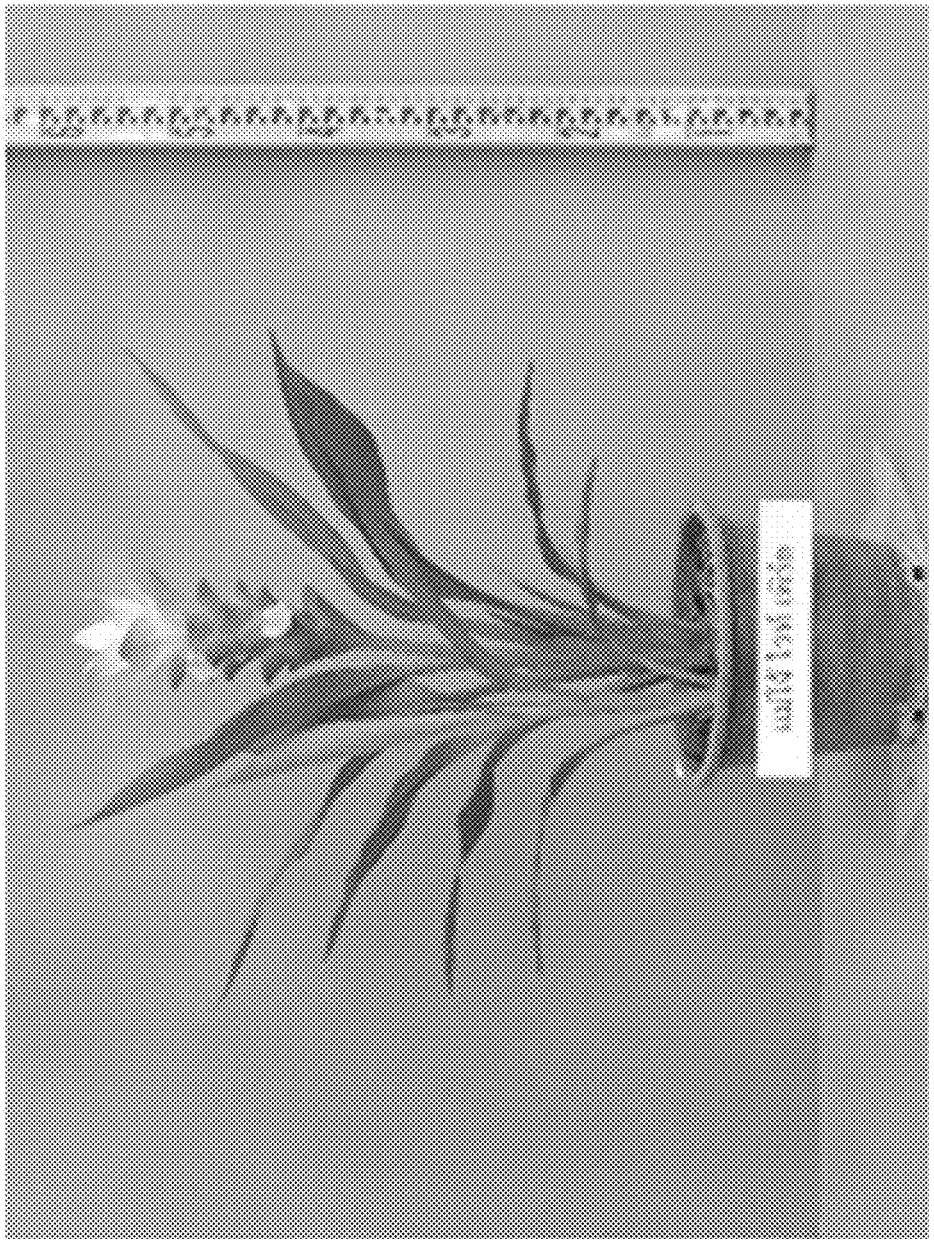
FIG. 1 illustrates a flowering plant of the new variety.
Figure 2:
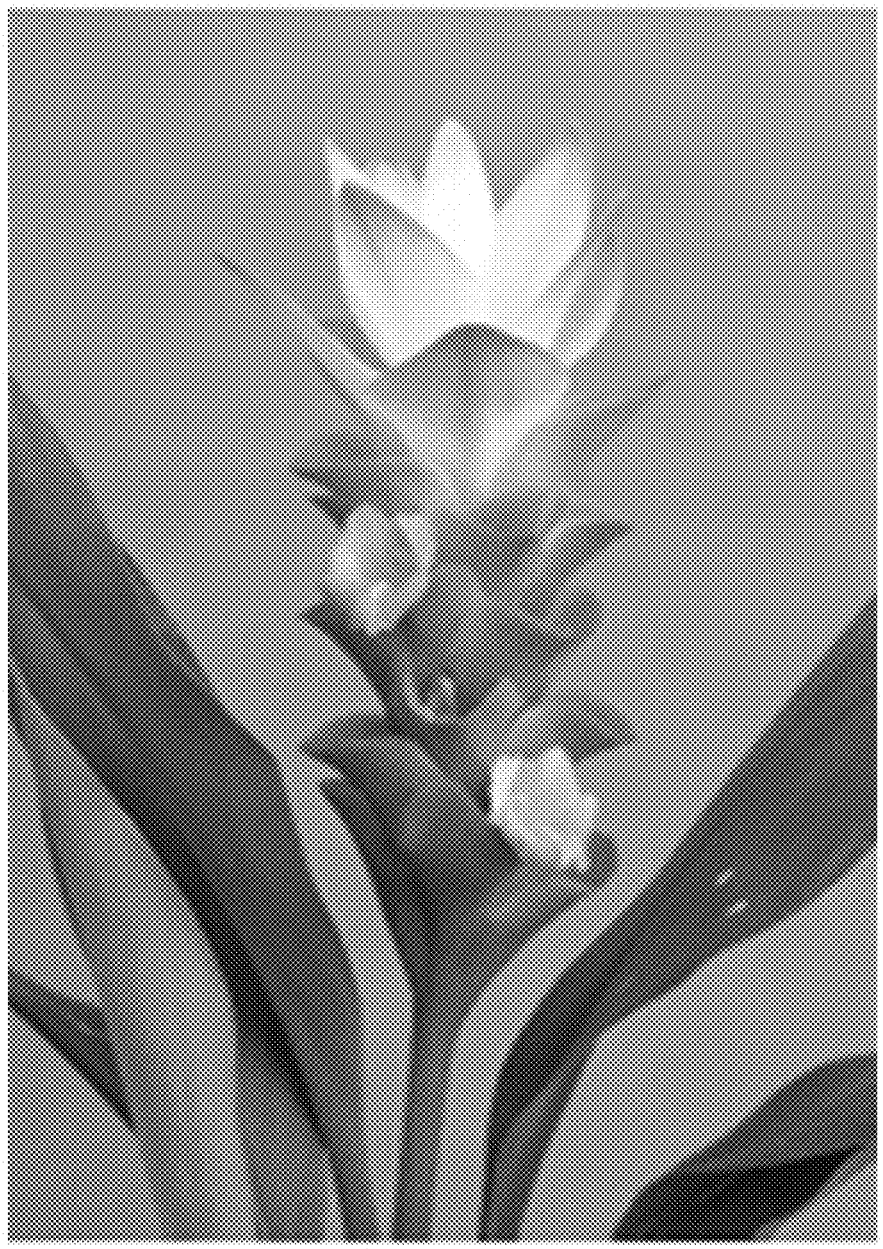
FIG. 2 is a close-up view of a typical inflorescence of the new variety.
Figure 3:
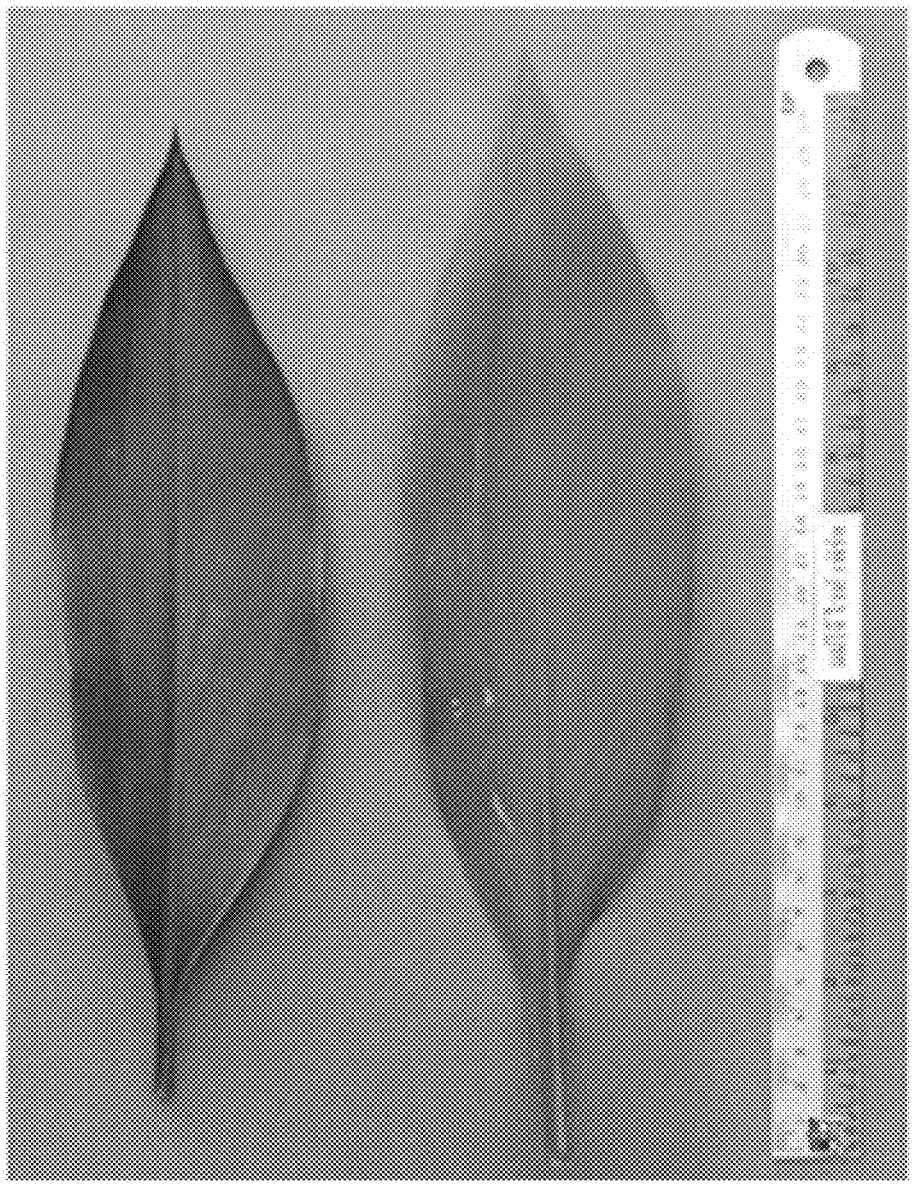
FIG. 3 is a close-up view of typical foliage of the new variety.
Figure 4:
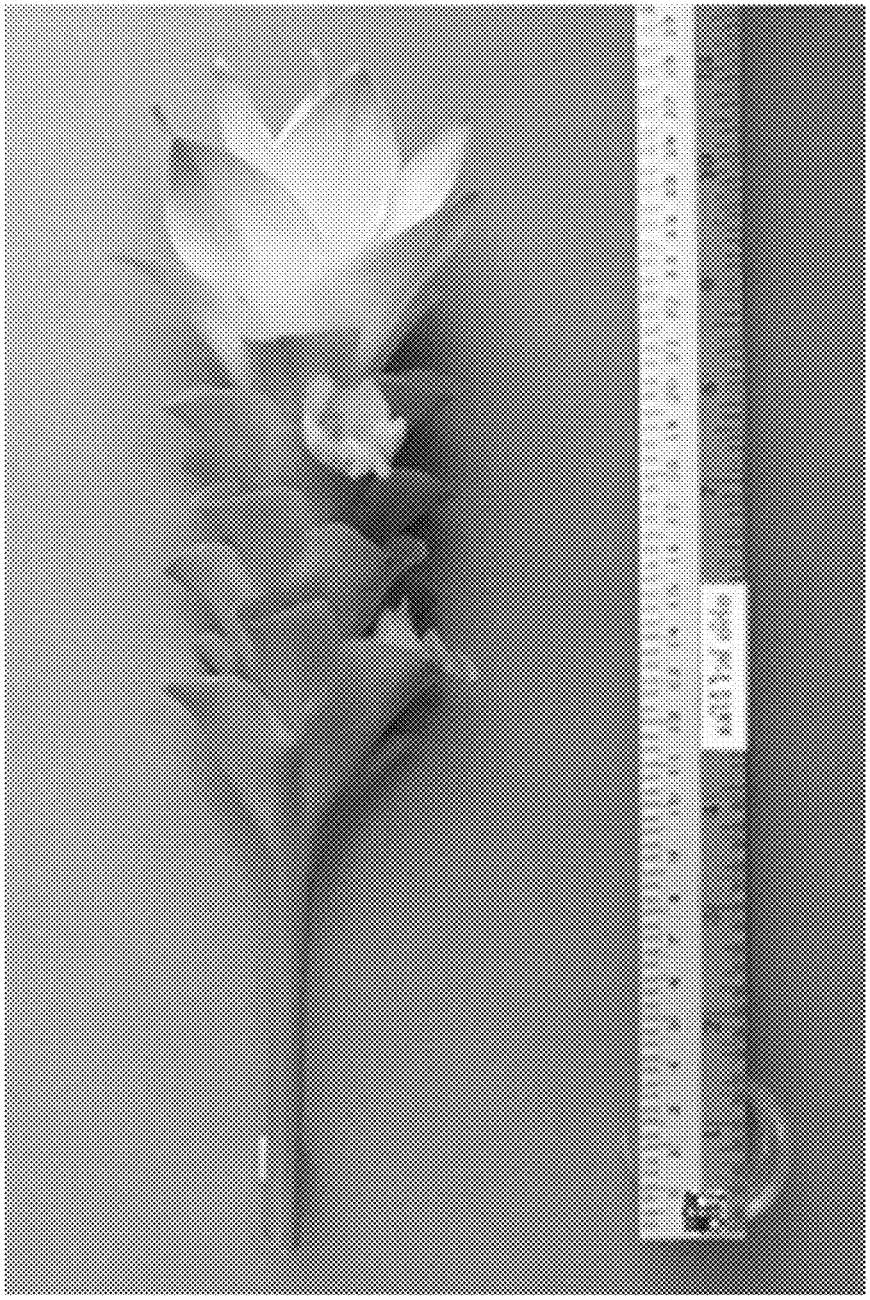
FIG. 4 is a close-up view of a typical inflorescence of the new variety, along with a ruler with centimeter units.

The following is a detailed description of the botanical characteristics of the new and distinct *Curcuma* 'Maejo White Pearl'. The detailed description was taken from a 2-year-old container grown plant in Chiang Mai Province, Thailand. All colors cited herein refer to The Royal Horticultural Society Colour Chart (R.H.S.), London, Sixth Edition. Where specific dimensions, sizes, colors, and other characteristics are given, it is to be understood that such characteristics are approximations or averages set forth as accurately as practicable.

Botanical classification: *Curcuma* 'Maejo White Pearl'.

PROPAGATION

Propagation method: Tissue culture.

Time to initiate roots: About 20 days at approximately 20-30° C.

Rooting habit: Moderately branching, medium density.

Root/rhizome description: Fibrous root with pale yellow color milk tank; color not accurately measured with R.H.S. chart. Number of storage roots per rhizome from 2 to 5 roots. Rhizome diameter 4 cm.

PLANT

Height: 50 to 60 cm.

Plant spread: 50.2 cm.

FOLIAGE

Leaf:

*Arrangement*.—Broad and alternate.

*Length*.—Average 35.5 cm.

*Width*.—Average 9.9 cm.

*Shape*.—Elliptic.

*Apex*.—Acurminate.

*Base*.—Narrow.

*Margin*.—Entire.

*Aspect*.—Initially upright, then about 45° from vertical.

*Texture*.—Top surface: Smooth, glabrous, matte. Bottom surface: Smooth, glabrous, matte.

*Color*.—Developing, upper side: RHS Green 138A. Developing, under side: RHS Green 138B. Fully expanded, upper side: RHS Green 137C. Fully expanded, under side: RHS Green 137C.

*Venation*.—Type: Pinnate and penninerved. Color: Near Green 143C upper and lower surfaces.

*Leaf sheaths*.—Length: Average 40 cm. Width: Average 5 cm. Texture: Top surface: Smooth, glabrous, moderately glossy. Bottom surface: Smooth, glabrous, slightly glossy. Color: Upper side: RHS Green 143B. Under side: RHS Green 143B. Venation: RHS Green 143C.

FLOWER

Inflorescence:

*Arrangement*.—Dense and upright terminal spike inflorescences developing directly from the basal shoots with numerous showy flower bracts; typically each spike with three flowers per bract; about 150 flowers developing per plant.

*Time to flower*.—In Thailand, plants begin flowering about 16 to 18 weeks after planting.

*Inflorescence longevity*.—Flowers last about 1 month on the plant if plants are well maintained.

*Fragrance*.—None.

*Length*.—About 20 cm.

*Diameter*.—About 10 cm.

Flowers:

*Length*.—About 4 cm.

*Diameter*.—About 2 cm.

*Arrangement*.—Zygomorphic with three petals fused towards the base; dorsal petal (labellum) is conspicuous and two smaller lateral petals; calyx with three sepals fused at the base.

Petals:

*Length, dorsal petal*.—About 4 cm.
*Length, lateral petals*.—About 3.5 cm.
*Width, dorsal petal*.—About 2 cm.
*Width, lateral petals*.—About 1 cm.
*Shape*.—Curved lanceolate.
*Color*.—From flowers in Upper Bracts, upper and lower surfaces: White 155B. From flowers in Lower Bracts, upper and lower surfaces: White 155B flushed Purple 76D.

Flower bracts:

*Quantity*.—About 10 upper bracts and about 20 lower bracts per inflorescence.
*Length, upper bracts*.—About 8 cm.
*Width, upper bracts*.—About 4 cm.
*Length, lower bracts*.—About 5 cm.
*Width, upper bracts*.—About 4 cm.
*Shape, upper bracts*.—Elliptic.
*Shape, lower bracts*.—Shallow U-shaped.
*Apex, upper bracts*.—Acute.
*Apex, lower bracts*.—Obtuse.
*Base, all bracts*.—Fused.
*Margin, upper bracts*.—Entire.
*Margin, lower bracts*.—Entire, undulate.
*Texture, upper bracts*.—Upper and lower surfaces smooth, glabrous, slightly glossy.
*Texture, lower bracts*.—Upper and lower surfaces smooth, glabrous; moderately glossy.
*Color*.—Upper bracts, upper surface: RHS white NN155D with green 143C margin; towards the apex, strongly tinged with green 143B. Lower bracts, upper surface: RHS Green 143B, margin 143C. Upper bracts, lower surface: RHS White NN155D with green143C and 143D margin; the apex, strongly tinged green 143B. Lower bracts, upper surface: RHS Green 143B, margin 143C.

Peduncles:

*Length*.—About 40 cm.
*Diameter*.—About 8 mm.
*Strength*.—Strong.
*Texture*.—Smooth, glabrous; moderately glossy.
*Angle*.—Upright, erect.
*Color*.—RHS Green 143B.

REPRODUCTIVE ORGANS

Pistils:

*Pistil number*.—1.
*Pistil length*.—About 4 cm.
*Style length*.—About 3 cm.
*Stigma shape*.—Club-shaped.
*Stigma diameter*.—About 1.5 mm.
*Stigma color*.—RHS Yellow-Green 145C.
*Ovary color*.—RHS Yellow-Green 145D.

Stamens:

*Stamen number*.—2 per flower.
*Filament length*.—About 1.2 cm.
*Filament diameter*.—About 2 mm.
*Filament color*.—RHS Yellow-Green 154D.
*Anther length*.—About 5 mm.
*Anther width*.—About 2 mm.
*Anther shape*.—Narrowly oblong.
*Anther color*.—RHS Yellow-Green 154C.
*Pollen amount*.—None.

OTHER CHARACTERISTICS

Fruit/seed: None.

Disease/pest resistance: Neither resistance nor susceptibility to the normal pests and diseases of *Curcuma* has been observed.

Temperature tolerance: 20° to 40° C. or tropical climate conditions.

Drought tolerance: Unknown.

What is claimed is:

1. A new and distinct cultivar of *Curcuma* plant named 'Maejo White Pearl', substantially as illustrated and described herein.

* * * * *